United States Patent [19]

Gilman

[11] Patent Number: 5,018,516
[45] Date of Patent: May 28, 1991

[54] DELIVERY SYSTEM FOR A WOUND DRESSING

[75] Inventor: Thomas H. Gilman, Mansfield, Mass.

[73] Assignee: The Kendall Company, Mansfield, Mass.

[21] Appl. No.: 455,535

[22] Filed: Dec. 22, 1989

[51] Int. Cl.$^5$ .................. A61F 13/00; A61F 15/00; A61L 15/00
[52] U.S. Cl. .................... 128/155; 128/156
[58] Field of Search .................. 128/156, 155

[56] References Cited

U.S. PATENT DOCUMENTS

| | | | |
|---|---|---|---|
| 2,969,057 | 1/1961 | Simmons | 128/155 |
| 3,888,247 | 6/1975 | Stenvall | 128/155 |
| 3,908,645 | 9/1975 | Sandvig | 128/156 |
| 4,334,530 | 6/1982 | Hassell | 128/156 |
| 4,545,372 | 10/1985 | Lauritzen | 128/156 |
| 4,832,008 | 5/1989 | Gilman | 128/154 |

Primary Examiner—David J. Isabella
Assistant Examiner—A. Paul Zuttarelli
Attorney, Agent, or Firm—Alvin Tsaacs

[57] ABSTRACT

A delivery system for a wound dressing comprising, an elastomeric film having a front surface, a back surface, an adhesive on the front surface, a first end margin, and a second opposed end margin, with the film having a pressure-sensitive adhesive on the front surface. The system has a release sheet releasably attached to and covering the adhesive on the film. The system has a tab member secured to the back surface of the film adjacent to the first end margin. The system also has a support sheet releasably attached to the back surface of the film, with the support sheet having a first end margin located adjacent to the tab member and being free of attachment to the tab member, and a second end margin located adjacent to the second end margin of the film.

4 Claims, 1 Drawing Sheet

DELIVERY SYSTEM FOR A WOUND DRESSING

BACKGROUND OF THE INVENTION

The present invention relates to wound dressings, and more particularly to delivery systems for such wound dressings.

Before the present invention, wound dressings for curing the wound of a patient were known, such as POLYSKIN, a trademark of The Kendall Company, Boston, Massachusetts. However, such wound dressings may not be self supporting, and may inadvertently wrinkle when applied to the patient. Hence, it is desirable to provide a delivery system for the dressing to facilitate its application without wrinkling of the dressing. Some delivery systems have been proposed, but are complex in structure, and are confusing to use.

SUMMARY OF THE INVENTION

A principle feature of the present invention is the provision of an improved delivery system for a wound dressing.

The delivery system of the present invention comprises, an elastomeric film having a front surface, a back surface, an adhesive on the front surface, a first end margin, and a second opposed end margin. The system has a release sheet releasably attached to and covering the adhesive on the film, and a tab member secured to the back surface of the film adjacent to the first end margin. The system has a support sheet releasably attached to the back surface of the film, with the support sheet having a first end margin located adjacent the tab member and being free of attachment to the tab member, and a second end margin located adjacent the second end margin of the film.

A feature of the present invention is that the support sheet provides support for the film, and prevents possible wrinkling of the film during application of the system.

Thus, a feature of the present invention is that the support sheet facilitates application of the film on a patient over a wound.

Another feature of the present invention is that the second end margin of the support sheet may be grasped in order to peel the film from the release sheet in a simplified manner.

Yet another feature of the invention is that the film may then be applied to the patient's skin with the support sheet in place on the film in order to facilitate application of the film without the possibility of wrinkling.

Still another feature of the invention is that after application of the film on the patient, the first end margin of the support sheet may be grasped in order to peel the support sheet from the film in a simplified manner, and this process does not disrupt the adhesive bond between the dressing and the skin.

A further feature of the invention is that the tab member facilitates the placement of the film by the system on the patient.

Another feature of the invention is that the tab member provides an edge which permits easy removal of the film when it is desired to peel it from the patient.

Still another feature of the invention is that the tab member provides a surface on which the user may write suitable legend.

An important feature of the invention is that the support sheet includes indicia bearing members on the first and second margins to indicate the sequence of manipulation of the support member, thus providing a system that is easy to use.

Thus, a feature of the present invention is that the system permits placement of the film on a patient's skin in a simplified manner.

Yet another feature of the present invention is that the system is of simplified construction and reduced cost.

Further features will become more fully apparent in the following description of the embodiments of this invention and from the appended claims.

DESCRIPTION OF THE PREFERRED EMBODIMENTS

Figure 1:
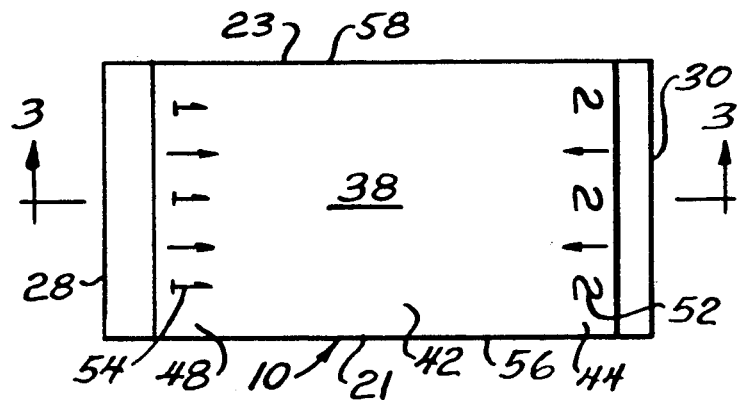
FIG. 1 is a top plan view of a delivery system for a wound dressing of the present invention.
Figure 2:
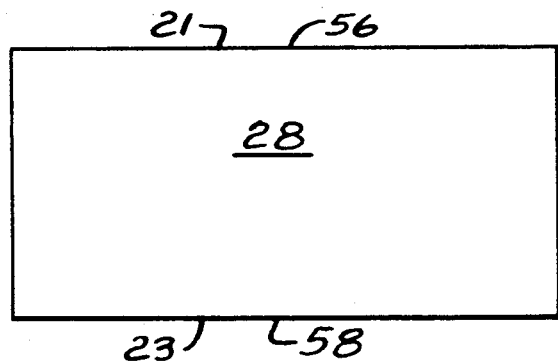
FIG. 2 is a lower plan view of the system of FIG. 1.
Figure 3:
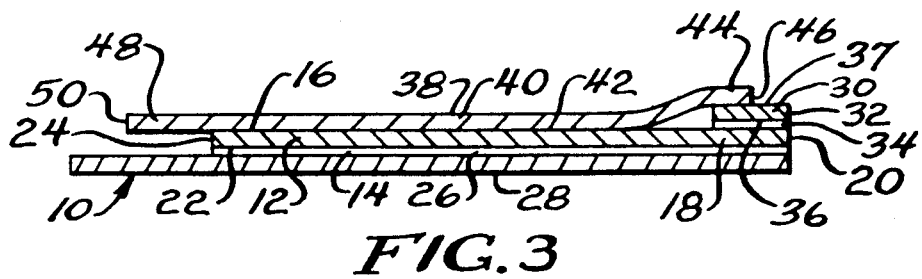
FIG. 3 is a sectional view taken substantially as indicated along the line 3—3 of FIG. 1.

Referring now to FIGS. 1-3, there is shown a delivery system generally designated 10 for a wound dressing or film 12. The film 12 comprises a suitable elastomeric material, such as polyurethene. The film has a front surface 14, a back or rear surface 16, a first end margin 18 defining a first end edge 20, a second end margin 22 defining a second edge 24, and a pressure sensitive adhesive, such as an acrylic or rubber based adhesive, covering the front surface 14 of the film 12, and may assume the form of the dressing POLYSKIN, a trademark of The Kendall Company, Boston, MA. The film 12 also has a pair of opposed side edges 21 and 23 connecting the end edges 20 and 24. As shown, the system 10 has a release sheet or release liner 28 releasably attached to and covering the adhesive 26 of the film 12. The release sheet 28 may assume a suitable form known to the art, such as a strip of paper having a silicone release coating facing the adhesive 26.

The system 10 has a tab member 30 having an outer end edge 32. The tab member 30 has a pressure-sensitive adhesive 34 on a front surface 36 of the tab member 30 in order to secure the tab member 30 onto the back surface 16 of the film 12, with the end edge 32 of the tab member 30 being generally aligned with the first end edge 20 of the film 12.

The system 10 has a support sheet 38 for the film 12. The support sheet 38 may be constructed from any suitable material which would be more stiff than the film 12, such as a relatively stiff plastic film, e.g. ethylene vinyl acetate, or paper. The support sheet 38 has a front surface 42, a back or rear surface 40, a first end margin 48 defining a first end edge 50, a second end margin 44 defining a second end edge 46, and a pair of opposed side edges 56 and 58 connecting the end edges 46 and 50.

The support sheet 38 has a first indicia region 54 on the back surface 42 of the support sheet 38 in the first end margin 48 by suitable means, such as adhesive. The support sheet 38 also has a second indicia region 52 on the back surface 42 of the support sheet 38 in the second end margin 44. As will be discussed further below, the first indicia region 54 indicates a first manipulation of the support sheet 38, and may be designated by indicia "1" on the region 54, as shown, while the second indicia region 52 indicates a second manipulation of the support sheet 38, and may be designated by indicia "2" on the region 52, as shown. The second end margin 44 of the support sheet 38 is free of attachment from the tab member 30, although at least a portion of the second end margin 44 of the support sheet 38 overlies a back surface 37 of the tab member 30, with the second end edge 46 of the support sheet 38 preferably being located over the tab member 30. The front surface 42 of the support sheet 38 is thermobonded to the back surface 16 of the film 12 in order to releasably attach the support sheet 38 to the film 12.

Figure 4:
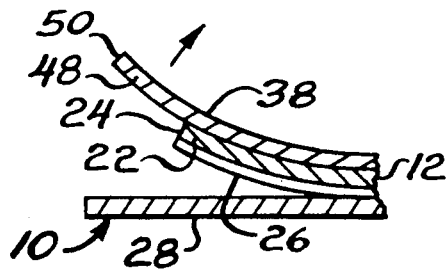
FIG. 4 is a fragmentary sectional view illustrating the manipulation of a support sheet of the system in order to remove a film from a release sheet.

In use, the first end margin 48 of the support sheet 38 is grasped and pulled, as shown in FIG. 4 in order to remove the adhesive 26 of the film 12 from the release sheet 28. This manipulation of the support sheet 38 is indicated by the first indicia region 54 on the support sheet 38. In this manner, the release sheet 28 is removed in a simplified manner from the film 12 in order to render the dressing or film 12 in a condition for application to the skin of a patient over a wound with the support sheet 38 providing the necessary support for the film 12 during application such that the film 12 may be applied without the possibility of wrinkling. During this time, the tab member 30, which is stiffer than the film, provides rigidity and support for the first end margin 18 of the film 12.

Figure 5:
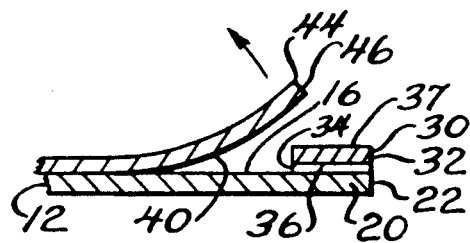
FIG. 5 is a fragmentary sectional view illustrating the manipulation of the support sheet to remove it from the film.

After application of the film 12 on the patient, the second end margin 44 of support sheet 38 is grasped, as shown in FIG. 5, over the tab member 30 in order to peel the support sheet 38 from the film 12 in a simplified manner, after which the support sheet 38 may be discarded leaving the film 12 in place on the patient. This manipulation is indicated by the second indicia region 52 on the support sheet 38. In addition, the tab member 30 provides a surface on which legends can be written by the user, and it also provides an edge for easy removal of the film 12 from the patient when it is desired to peel the film from the patient.

Thus, in accordance with the present invention, the system 10 permits the application of the film or dressing 12 in a simplified manner. Also, the system 10 provides support by the support sheet 38 to the film 12 during application of the film 12 in order to prevent wrinkling of the film 12.

The foregoing detailed description is given for clearness of understanding only and no unnecessary limitations should be understood therefrom, as modifications will be obvious to those skilled in the art.

I claim:

1. A delivery system for applying a wound dressing comprising:
   an elastomeric film wound dressing characterized by not being self-supporting and as having a tendency towards inadvertent wrinkling when attempting to apply the dressing to the wound, the film having a front surface, a back surface, a first end margin defining a first end edge and a second end margin defining a second end edge;
   a pressure-sensitive adhesive layer on the front surface of the film;
   a release sheet releasably attached to and covering the adhesive layer on the film;
   a tab member secured to the second end margin of the film on the back surface of the film, the tab member having an end edge generally aligned with the second end edge of the film;
   a support sheet having a front surface, a back surface, a first end margin defining a first end edge, a second end margin defining a second end edge, the support sheet having its front surface releasably secured to the back surface of the film, the second end edge of the support sheet being located over the tab member with the support sheet being free of attachment from the tab member;
   and first and second indicating strips secured to the back surface of the support sheet in the first and second margins of the support sheet with the first indicating strip including a first means indicating a first manipulation for separating the film from the release sheet for applying the dressing to the wound without wrinkling and the second indicating strip including a second means signifying a second manipulation to peel the support sheet from the back of the film after the dressing has been applied to the wound.

2. A delivery system as defined in claim 1 wherein the first end margin of the support sheet extends past the first end margin of the film.

3. A delivery system as defined in claim 1 wherein the support sheet is heat bonded to the film.

4. A delivery system as defined in claim 1 wherein the tab member has adhesive on a front surface thereof securing the tab member to the back surface of the film.

* * * * *